United States Patent
Kopalli

(10) Patent No.: US 11,944,755 B2
(45) Date of Patent: Apr. 2, 2024

(54) METHODS AND SYSTEM FOR OXYGEN SENSOR PROGNOSTICS IN A MEDICAL GAS FLOW DEVICE

(71) Applicant: GE Precision Healthcare LLC, Milwaukee, WI (US)

(72) Inventor: Chandra Aloke Kopalli, Bangalore (IN)

(73) Assignee: GE Precision Healthcare LLC, Milwaukee, WI (US)

( * ) Notice: Subject to any disclaimer, the term of this patent is extended or adjusted under 35 U.S.C. 154(b) by 892 days.

(21) Appl. No.: 16/854,796

(22) Filed: Apr. 21, 2020

(65) Prior Publication Data

US 2021/0322709 A1 Oct. 21, 2021

(51) Int. Cl.
*A61M 16/10* (2006.01)
*A61M 16/00* (2006.01)
*A61M 16/01* (2006.01)

(52) U.S. Cl.
CPC .... *A61M 16/1005* (2014.02); *A61M 16/0051* (2013.01); *A61M 16/01* (2013.01); *A61M 16/024* (2017.08); *A61M 2016/1025* (2013.01)

(58) Field of Classification Search
CPC ............ A61M 16/1005; A61M 16/101; A61M 16/1015; A61M 16/024; A61M 16/022; A61M 16/026; A61M 16/0051; A61M 16/01; A61M 16/021; G01N 33/497; G01N 33/0006; G01N 33/007; G01N 27/30; G01N 27/409; G01N 27/404; G01N 27/4163; G01N 27/4175
See application file for complete search history.

(56) References Cited

U.S. PATENT DOCUMENTS

| | | | | |
|---|---|---|---|---|
| 4,779,446 A | * | 10/1988 | Rowland | G01R 31/3648 205/785.5 |
| 2004/0107965 A1 | * | 6/2004 | Hickle | A61M 16/085 128/204.22 |
| 2014/0188402 A1 | * | 7/2014 | Garcia | G01N 33/48792 702/23 |
| 2020/0103387 A1 | * | 4/2020 | Brown | G01N 33/0073 |
| 2020/0297960 A1 | * | 9/2020 | O'Donnell | A61M 16/0063 |
| 2020/0368464 A1 | * | 11/2020 | Brunetto Tancredi | A61M 16/0003 |

(Continued)

FOREIGN PATENT DOCUMENTS

| CN | 102116760 A | * | 7/2011 |
|---|---|---|---|
| JP | 2001305092 A | * | 10/2001 |
| JP | 4540021 B2 | * | 9/2010 |

OTHER PUBLICATIONS

Machine English Translation of CN-102116760-A provided by PE2E (Year: 2011).*

(Continued)

*Primary Examiner* — Joseph D. Boecker
*Assistant Examiner* — Brian T Khong

(57) ABSTRACT

Methods and systems are provided for an oxygen sensor included in a medical gas flow device, such as an anesthesia machine. In one embodiment, a method for a medical gas flow device comprises tracking an output voltage of an oxygen sensor during calibration over time, and, responsive to the output voltage decreasing by at least threshold amount from an initial calibration output voltage, estimating an end-of-life date of the oxygen sensor and outputting a replacement notification.

15 Claims, 5 Drawing Sheets

(56) References Cited

U.S. PATENT DOCUMENTS

2021/0209497 A1* 7/2021 Wang .................... G06N 7/005
2022/0331533 A1* 10/2022 Wan ..................... A61M 16/12

OTHER PUBLICATIONS

Machine English Translation of JP-2001305092-A provided by PE2E (Year: 2001).*

English Machine Translation of JP-4540021-B2 provided by PE2E (Year: 2010).*

* cited by examiner

METHODS AND SYSTEM FOR OXYGEN SENSOR PROGNOSTICS IN A MEDICAL GAS FLOW DEVICE

FIELD

Embodiments of the subject matter disclosed herein relate to systems and methods for an oxygen sensor in a medical device.

BACKGROUND

Some types of medical equipment, such as ventilators and anesthesia machines, may include an advanced breathing system for moving breathable gas into and out of a patient's lungs. The advanced breathing system may include a sensor for monitoring a concentration of oxygen in the breathable gas delivered to the patient. In some examples, the sensor may be an electrochemical oxygen sensor that generates an electrical voltage in proportion to the concentration of oxygen in the breathable gas until a working electrode of the sensor is depleted. In other medical equipment, including incubators, an environment with oxygen concentration more than 21% (air) is provided around the patient, and the electrochemical oxygen sensor may be used to monitor and control the concentration of oxygen in the environment around the patient.

BRIEF DESCRIPTION

In one embodiment, a method for a medical gas flow device comprises tracking an output of an oxygen sensor during calibration over time, and, responsive to the output decreasing by at least a threshold amount from an initial calibration output, estimating an end-of-life date of the oxygen sensor and outputting a replacement notification. In this way, the oxygen sensor may be replaced in a timely manner, reducing an occurrence of premature replacements and also reducing an occurrence of unpredicted replacements.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
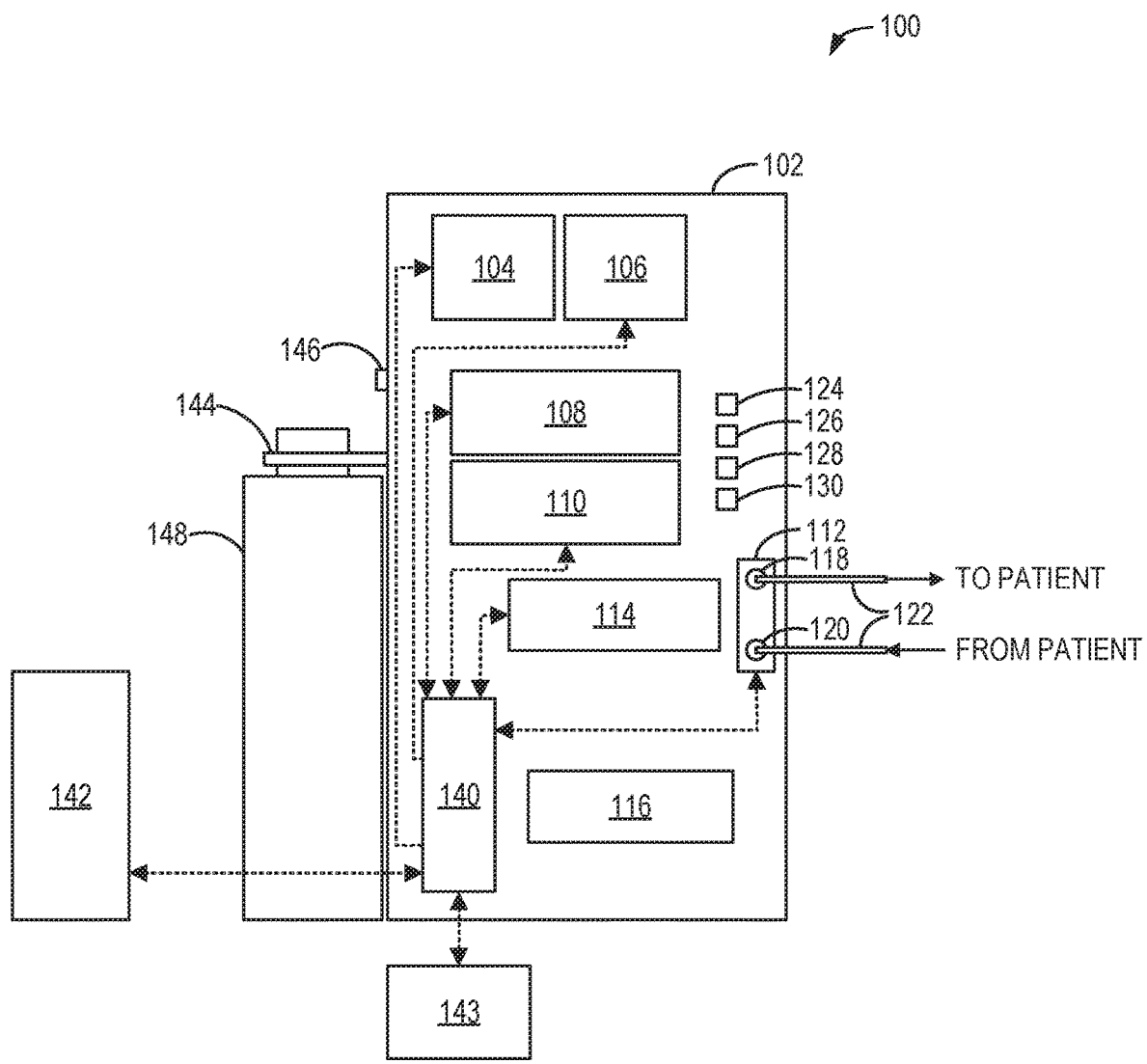
FIG. 1 schematically shows an anesthesia machine, according to an embodiment.
Figure 3:
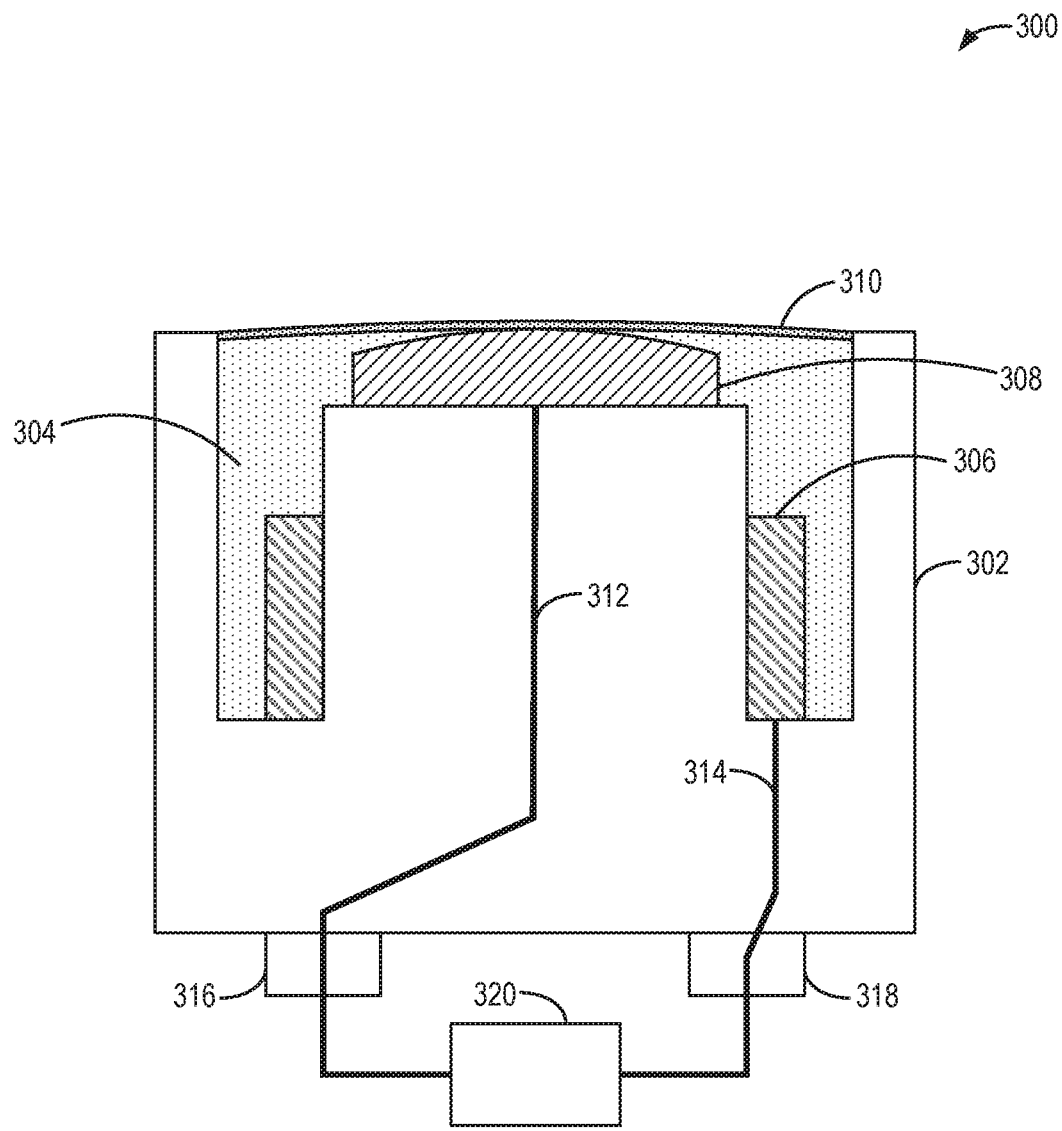
FIG. 3 schematically shows an oxygen sensor that may be included in the advanced breathing system of FIG. 2, according to an embodiment.
Figure 4:
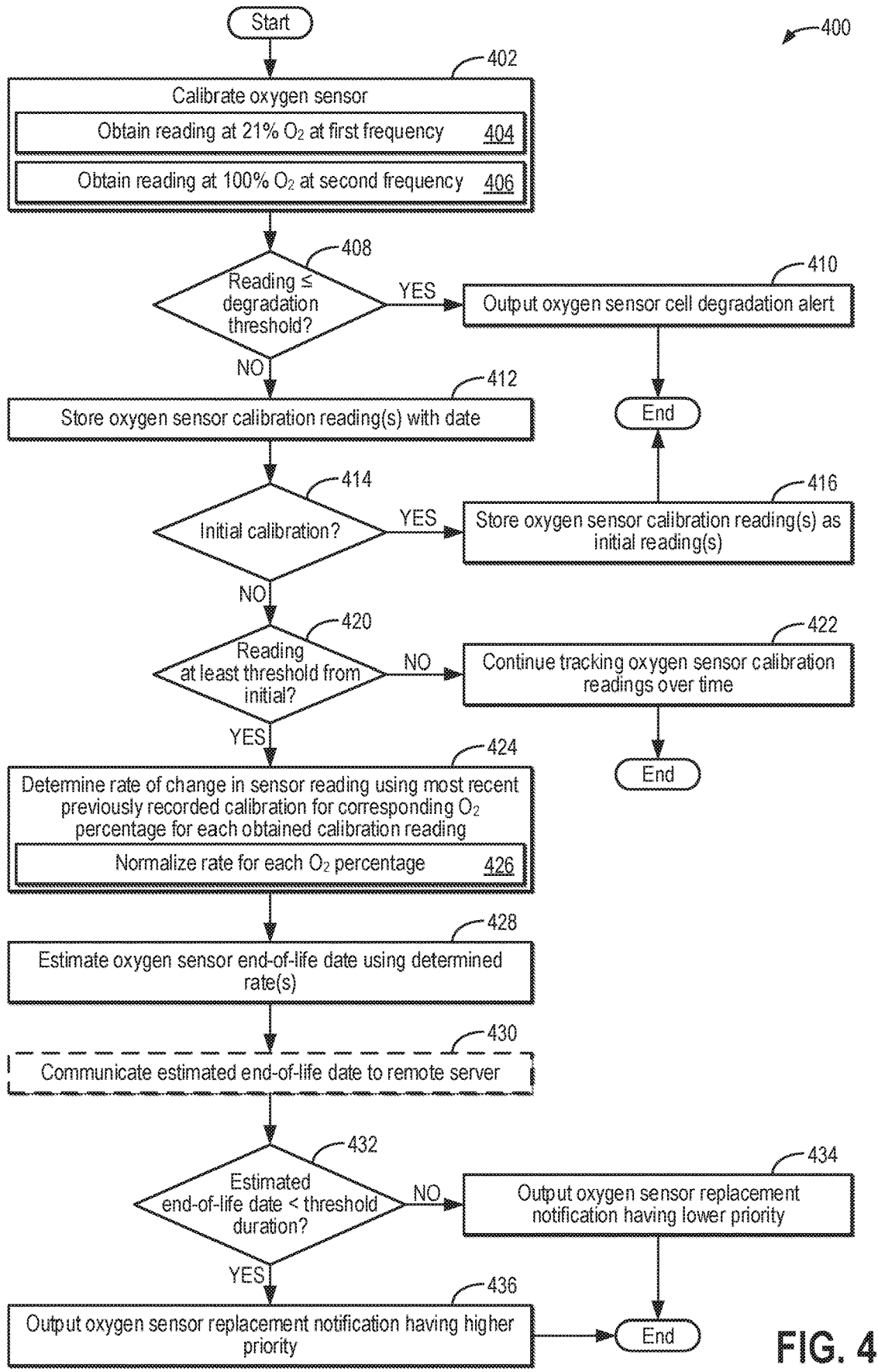
FIG. 4 shows a flow chart of an example method for monitoring an oxygen sensor in a medical device and estimating an end-of-life date, according to an embodiment.
Figure 5:
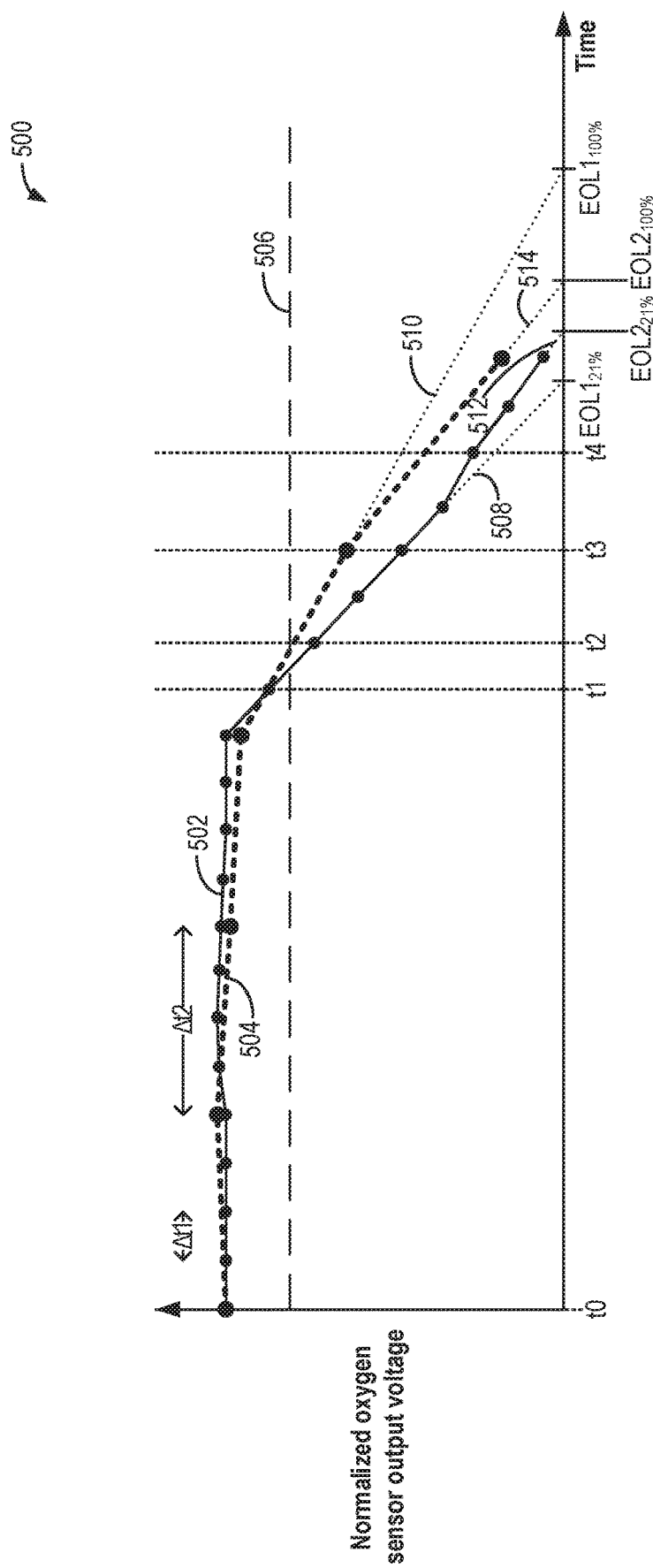
FIG. 5 shows an example graph of tracking calibration measurements of an oxygen sensor over time to estimate an end-of-life date, according to an embodiment.

The following description relates to various embodiments for an oxygen sensor in a medical gas flow device, which may be an anesthesia machine, for example, such as the example anesthesia machine shown in FIG. 1. The anesthesia machine may include an advanced breathing system, such as the example advanced breathing system shown in FIG. 2, to deliver a medical gas to a patient. The advanced breathing system may include a variety of sensors, including an oxygen sensor, to monitor a composition of the medical gas delivered to the patient. FIG. 3 schematically shows a cross-sectional view an example oxygen sensor that may be included in the advanced breathing system of FIG. 2. In particular, the oxygen sensor shown in FIG. 3 is an electrochemical, fuel cell-type oxygen sensor having an anode that becomes oxidized over time as the oxygen sensor is exposed to oxygen. The oxidation of the anode results in a change in an output voltage of the oxygen sensor over time until the anode is fully oxidized and the oxygen sensor is no longer functional. Therefore, FIG. 4 provides an example method for estimating an end-of-life date of the oxygen sensor. For example, a controller may use oxygen sensor calibration methods to track a change in the output voltage and relate the change in the output voltage to an estimated end-of-life date, an example of which is illustrated in FIG. 5. The estimated end-of-life date may be a date by which oxygen sensor replacement is recommended and may be communicated to an operator of the medical gas flow device, for example. In this way, a replacement may be procured before the oxygen sensor stops functioning.

Advantages that may be realized in the practice of some embodiments of the described systems and techniques are that, by prompting ordering of a replacement oxygen sensor based on the estimated end-of-life date, an oxygen sensor may be used in a medical gas flow device until substantially depleted without risking downtime of the medical gas flow device due to unexpected oxygen sensor depletion. Further, shelf storage times of the replacement oxygen sensor may be decreased, as the replacement order may be timed with increased accuracy versus, for example, averaging oxygen replacement times. For example, the average oxygen sensor replacement time may not accurately reflect a duration before an oxygen sensor becomes depleted due to the unique oxygen exposure conditions of each oxygen sensor. Because oxygen sensors are sensitive to storage conditions, such as temperature, reducing shelf storage may reduce oxygen sensor degradation. By accurately estimating an end-of-life date of an oxygen sensor and prompting replacement ordering accordingly, oxygen sensor costs may be decreased. Overall, user satisfaction may be increased.

Turning now to the figures, FIG. 1 schematically shows an embodiment of a medical gas flow device. In the embodiment shown, the medical gas flow device is an anesthesia machine 100. Anesthesia machine 100 includes a frame (or housing) 102. In some embodiments, frame 102 may be supported by casters, where the movement of the casters may be controlled (e.g., stopped) by one or more locks. In some examples, the frame 102 may be formed of a plastic material (e.g., polypropylene). In other examples, the frame 102 may be formed of a different type of material (e.g., metal, such as steel).

Anesthesia machine 100 also includes an anesthesia display device 104, a patient monitoring display device 106, a respiratory gas module 108, one or more patient monitoring modules, such as a patient monitoring module 110, an advanced breathing system (ABS) 112 (explained in more detail below), an anesthetic vaporizer 114, and an anesthetic agent storage bay 116. Anesthesia machine 100 may further include a main power indicator 124, a system activation switch 126 (which, in one example, permits gas flow when activated), an oxygen flush button 128, and an oxygen control 130. Anesthetic vaporizer 114 may vaporize anesthetic agent and combine the vaporized anesthetic agent with one or more medical grade gases (e.g., oxygen, air, nitrous oxide, or combinations thereof), which may then be delivered to a patient.

Anesthesia machine 100 may additionally include an integrated suction, an auxiliary oxygen flow control, and various other components for providing and/or controlling a flow of the one or more medical grade gases to the patient. For example, anesthesia machine 100 includes one or more pipeline connections 146 to facilitate coupling of the anesthesia machine to pipeline gas sources. Additionally, anesthesia machine 100 includes a cylinder yoke 144, via which one or more gas-holding cylinders 148 may be coupled to the anesthesia machine. Thus, through the pipeline connection and/or cylinder connections, gas may be provided to the anesthesia machine, where the gas may include (but is not limited to) medical air, oxygen, nitrogen, and nitrous oxide. The gas that enters the anesthesia machine may mix with the vaporized anesthetic agent at the anesthetic vaporizer 114, as described above, before being supplied to a patient via the ABS 112. The anesthesia machine may also include a serial port, a collection bottle connection, a cylinder wrench storage area, and an anesthetic gas scavenging system.

In some embodiments, the ABS 112 may include an expiratory check valve at an expiratory port 120, an expiratory flow sensor at the expiratory port 120, an inspiratory check valve at an inspiratory port 118, an inspiratory flow sensor at the inspiratory port 118, an absorber canister, a manual bag port, a ventilator release, an adjustable pressure-limiting valve, a bag/vent switch, and a bellows assembly. When a patient breathing circuit is coupled to the ABS 112, breathing gases (e.g., air, oxygen, and/or nitrous oxide mixed with vaporized anesthetic agent) exit the anesthesia machine from the inspiratory port 118 and travel to the patient. Expiratory gases from the patient re-enter the anesthesia machine via the expiratory port 120, where carbon dioxide may be removed from the expiratory gases via the absorber canister. An example embodiment of an advanced breathing system will be described below with respect to FIG. 2.

During operation of the anesthetic vaporizer 114, an operator (e.g., an anesthesiologist) may adjust an amount of vaporized anesthetic agent that is supplied to the patient by adjusting a flow rate of gases from the gas source(s) (e.g., the pipeline gas supply) to the vaporizer. The flow rate of the gases from the gas source to the vaporizer may be adjusted by the operator via adjustment of one or more flow adjustment devices. For example, the flow adjustment devices may include analog and/or digital adjustment dials and/or other user input devices configured to actuate one or more flow control valves of anesthesia machine 100. In some embodiments, a first flow control valve may be positioned between the gas source(s) and the anesthetic vaporizer 114 and may be actuatable via the flow adjustment devices to a fully opened position, a fully closed position, and a plurality of positions between the fully opened position and the fully closed position.

Anesthesia machine 100 may additionally include one or more valves configured to bypass gases from the gas source(s) around the anesthetic vaporizer 114. The valves may enable a first portion of gases to flow directly from the gas source to the inspiratory port 118 and a second portion of gases to flow from the gas source through the anesthetic vaporizer 114 to mix with the vaporized anesthetic agents prior to flowing to the inspiratory port 118. By adjusting a ratio of the first portion of gases relative to the second portion of gases, the operator may control a concentration of vaporized anesthetic agent administered to the patient via the inspiratory port 118.

Further, the adjustments described above may be facilitated at least in part based on output from the respiratory gas module 108. The respiratory gas module 108 may be configured to measure various parameters of the gases exiting the vaporizer and/or being provided to the patient. For example, the respiratory gas module 108 may measure the concentrations of carbon dioxide, nitrous oxide, and the anesthetic agent provided to the patient. Further, the respiratory gas module 108 may measure respiration rate, minimum alveolar concentration, patient oxygen, and/or other parameters. The output from the respiratory gas module 108 may be displayed via a graphical user interface on a display device (e.g., the anesthesia display device 104 and/or the patient monitoring display device 106) and/or used by a controller to provide closed-loop feedback control of the amount of anesthesia provided to the patient.

The ABS 112 may optionally be coupled to a breathing circuit (not shown) via one or more tubes (e.g., gas passages) 122. The breathing circuit may be coupled between an airway of a patient (e.g., via a breathing mask positioned to enclose the mouth and/or nose of the patient, or a tracheal intubation tube) and the inspiratory port 118 and the expiratory port 120. Gases (e.g., the one or more medical gases, or a mixture of the one or more medical gases and vaporized anesthetic agent from the anesthetic vaporizer 114) may flow from the inspiratory port 118, through the breathing circuit, and into the airway of the patient, where the gases are absorbed by the lungs of the patient. By adjusting the concentration of vaporized anesthetic agent in the gases as described above, the operator may adjust a degree to which the patient is anesthetized.

During conditions in which the breathing circuit is coupled to the airway, the anesthetic agent and/or fresh gas (without the anesthetic agent) may flow into the airway of the patient (e.g., through inhalation) via the inspiratory port 118 and the inspiratory check valve. As an example, the inspiratory check valve may open automatically (e.g., without input or adjustment by the operator) in response to inhalation by the patient and may close automatically in response to exhalation by the patient. Similarly, the expiratory check valve may open automatically in response to exhalation by the patient and may close automatically in response to inhalation by the patient.

In some embodiments, the operator may additionally or alternatively control one or more operating parameters of the anesthesia machine 100 via an electronic controller 140 of the anesthesia machine 100. The controller 140 includes a processor operatively connected to a memory. The memory may be a non-transitory computer-readable medium and may be configured to store computer executable code (e.g., instructions) to be processed by the processor in order to execute one or more routines, such as those described herein. The memory may also be configured to store data received by the processor. While controller 140 is shown positioned at a single location within anesthesia machine 100 in FIG. 1, it is to be understood that controller 140 may be located in various locations within, around, and/or remote from anesthesia machine 100. As an example, controller 140 may include multiple devices/modules that may be distributed throughout anesthesia machine 100. As such, controller 140 may include a plurality of controllers at various locations within anesthesia machine 100. As another example, additionally or alternatively, controller 140 may include one or more devices/modules that are external to anesthesia machine 100, located proximate to (e.g., in a same room) or remote from (e.g., a remote server) anesthesia machine 100. In each example, the multiple devices/modules may be communicatively coupled through wired and/or wireless connections.

Further, the controller 140 may be communicatively coupled (e.g., via wired or wireless connections) to one or more external or remote computing devices 142. As one example, the remote computing devices 142 may include a hospital computing system, and the controller 140 may be configured to share (e.g., send and receive) various information, such as electronic medical record information, procedure information, etc., with the remote computing devices 142. As another example, the remote computing devices 142 may additionally or alternatively include a remote monitoring server that logs status information regarding the anesthesia machine 100. For example, a manufacturer or other service provider (e.g., supplier) may remotely view the status information in order to anticipate maintenance requests and/or pre-emptively order replacement parts, as will be elaborated below with respect to FIG. 4. Thus, in some examples, the remote computing devices 142 may not be included a same location as anesthesia machine 100. The controller 140 may also be electronically coupled to various other components of the anesthesia machine 100, such as the anesthetic vaporizer 114, the ABS 112, the respiratory gas module 108, the anesthesia display device 104, and the patient monitoring display device 106.

The controller 140 receives signals from the various sensors of the anesthesia machine 100 and employs the various actuators of the anesthesia machine 100 to adjust operation of the anesthesia machine 100 based on the received signals and instructions stored on the memory of the controller. For example, the flow of gases to the inspiratory port 118 may be controlled at least in part from inputs received from a human-machine interface (HMI) 143 that is communicatively coupled to the electronic controller 140 of the anesthesia machine 100. For example, the HMI 143 may include a keyboard, a touchscreen, a mouse, and/or another type of input device that enables the operator to input commands or control parameters. The HMI 143 may also include one or more output devices, including a display screen, a speaker, etc., for communicating messages or other information to the operator. The controller 140 may display operating parameters of the anesthesia machine 100 via the anesthesia display device 104 and/or the patient monitoring display device 106. The controller may receive signals (e.g., electrical signals) via the HMI 143 and may adjust operating parameters of the anesthesia machine 100 in response (e.g., responsive) to the received signals.

As one example, the operator may input a desired concentration of the anesthetic agent to be delivered to the patient via the HMI 143. A corresponding valve position of one or more valves of the anesthesia machine (e.g., a position of one or more bypass valves, as described above) may be empirically determined and stored in a predetermined lookup table or function in a memory of the controller. For example, the controller may receive the desired concentration of the anesthetic agent via the input device and may determine an amount of opening of the one or more valves corresponding to the desired concentration of the anesthetic agent based on the lookup table, with the input being the concentration of the anesthetic agent and the output being the valve position of the one or more valves. The controller may transmit an electrical signal to an actuator of the one or more valves in order to adjust each of the one or more valves to the corresponding output valve position. In some examples, the controller may compare the desired flow rate of gases to a measured flow rate of gases, such as measured by the inspiratory flow sensor, for example.

Figure 2:
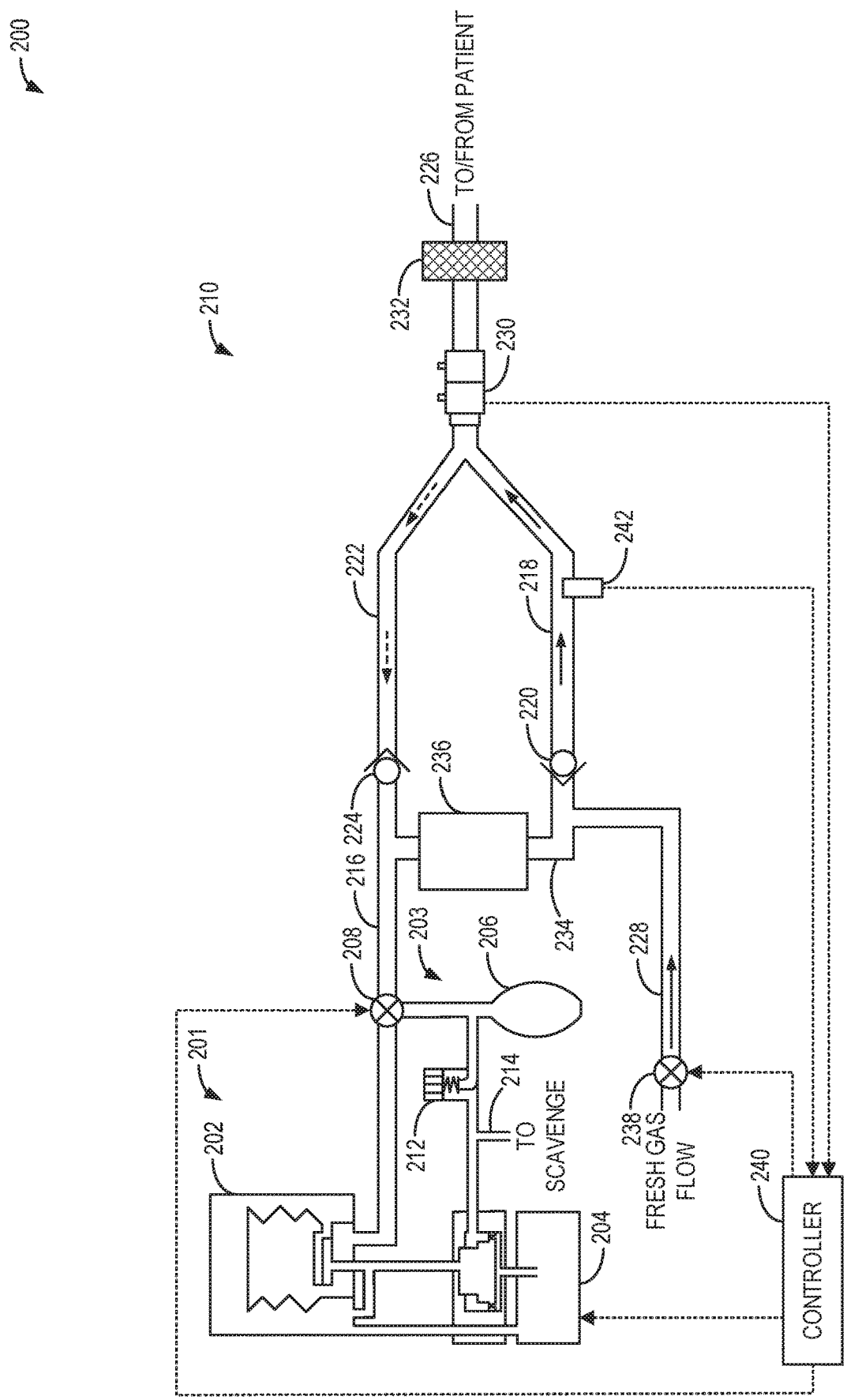
FIG. 2 schematically shows an advanced breathing system that may be included in the anesthesia machine of FIG. 1, according to an embodiment.

Next, FIG. 2 shows an exemplary embodiment of an advanced breathing system (ABS) 200. As one example, the ABS 200 may be the ABS 112 included in anesthesia machine 100 of FIG. 1. In other examples, the ABS 200 may be included in another medical gas flow system, such as an incubator. Further, the ABS 200 is one example configuration of an advanced breathing system, and other configurations are also possible that include at least one oxygen sensor, as will be elaborated below.

The ABS 200 includes two ventilation systems for providing gas (e.g., air, medical gases, and/or anesthetic agent) to a patient: an electronically operated ventilator 201 and a manually operated ventilator 203. The electronically operated ventilator 201 includes a bellows assembly 202 and a ventilator drive 204. The manually operated ventilator 203 includes a bag 206 and an adjustable pressure-limiting (APL) valve 212. A bag/ventilator switch 208 controls selection between the two ventilation systems. For example, when the manually operated ventilator 203 (e.g., bag ventilation) is selected at the bag/ventilator switch 208, the bag 206 and the APL valve 212 are connected to a circle breathing system 210 via a bidirectional gas passage 216, while the bellows assembly 202 and the ventilator drive 204 are disconnected. The bag 206 may be manually compressed by an operator of ABS 200 to pump gas through the circle breathing system 210. Further, waste gas from patient exhalation may exit the circle breathing system 210 via the APL valve 212 and may be directed to a scavenge system via a scavenge passage 214.

When the electronically operated ventilator 201 is selected at the bag/ventilator switch 208, the bag 206 and the APL valve 212 are disconnected from the bidirectional gas passage 216 and the circle breathing system 210, and the electronically operated ventilator 201 provides patient inspiration and expiration. For example, the ventilator drive 204 may be electronically controlled by a controller 240 (which may be part of the controller 140 of FIG. 1, for example) to pneumatically compress bellows within the bellows assembly 202 at a predetermined, adjustable rate. In addition, waste gas may exit the circle breathing system 210 via the bellows assembly 202 and the ventilator drive 204 and may be directed to the scavenge system via the same scavenge passage 214. The scavenge system may remove anesthetic agent so that it is not released into a treatment room (such as an operating theater, patient room, etc.).

The circle breathing system 210 includes a plurality of gas passages coupled to the bidirectional gas passage 216, including an inspiratory passage 218 having an inspiratory check valve 220 coupled therein, an expiratory passage 222 having an expiratory check valve 224 coupled therein, and a patient delivery passage 226 having an air flow sensor 230 and a filter 232 coupled therein. The patient delivery passage 226 may deliver the gas (e.g., air, medical gases, and or anesthetic agent) from the selected ventilation system to the patient during inhalation (e.g., via the inspiratory passage 218 and the inspiratory check valve 220) and may deliver waste gas from the patient to the scavenge system during exhalation (e.g., via the expiratory passage 222 and the expiratory check valve 224). The air flow sensor 230 may measure a flow rate through patient delivery passage 226 during both inhalation and exhalation. However, in other examples, a separate inhalation flow sensor and a separate exhalation flow sensor may be included, such as one air flow sensor coupled in the inspiratory passage 218 and another air flow sensor coupled in the expiratory passage 222.

In the example shown in FIG. 2, a gas passage 234 couples the inspiratory passage 218 to the expiratory passage 222 and includes an absorber canister 236 coupled therein. That is, the gas passage 234 is coupled to the inspiratory passage 218 upstream of the inspiratory check valve 220 and is coupled to the expiratory passage 222 downstream of the expiratory check valve 224. The inspiratory check valve 220 is a one-way valve that automatically opens in response to inhalation by the patient and closes automatically in response to exhalation by the patient. The inspiratory check valve 220 enables gas to flow from bidirectional gas passage 216 to the patient delivery passage 226 (e.g., via the gas passage 234 and the inspiratory passage 218) and blocks (e.g., prevents) gas flow from the patient delivery passage 226 to the gas passage 234. Similarly, the expiratory check valve 224 is a one-way valve that automatically opens in response to exhalation by the patient and closes automatically in response to inhalation by the patient. The expiratory check valve 224 enables gas to flow from the patient delivery passage 226 to the bidirectional gas passage 216 and blocks gas flow from the bidirectional gas passage 216 to the patient delivery passage 226 via the expiratory passage 222. Thus, all gas that flows to the patient flows through the inspiratory passage 218, and all gas that flows from the patient flows through the expiratory passage 222. Waste gas exhaled by the patient may flow back to the selected ventilation system (via the patient delivery passage 226 and the expiratory passage 222), where it may be recycled.

An oxygen sensor 242 is coupled to the inspiratory passage 218 and configured to measure an amount (e.g., concentration or percentage) of oxygen in the gas flowing to the patient. According to the embodiments described herein, the oxygen sensor 242 is an electro-galvanic oxygen sensor that produces an electrical output (e.g., an output voltage) in the presence of oxygen, as will be elaborated herein with respect to FIG. 3. Therefore, the controller 240 may determine the concentration of oxygen in the gas flowing to the patient via the patient delivery passage 226 based on the output voltage of the oxygen sensor 242. While FIG. 2 shows the oxygen sensor 242 positioned downstream of the inspiratory check valve 220, in other examples, the oxygen sensor 242 is positioned upstream of the inspiratory check valve 220, such as between a fresh gas inlet 228 and the inspiratory check valve 220. Other placements of the oxygen sensor 242 within the ABS 200 are also possible without parting from the scope of this disclosure. For example, the oxygen sensor 242 may be positioned at any location that enables monitoring of the concentration of oxygen delivered to the patient.

The fresh gas inlet 228 is positioned between the absorber canister 236 and the inspiratory check valve 220 so that a flow of gas provided to the patient on inspiration may include a mixture of enriched fresh gas (e.g., from an anesthetic vaporizer, such as anesthetic vaporizer 114 of FIG. 1) and scrubbed gas returned from the bag 206 or the bellows assembly 202 (depending on the position of the bag/ventilator switch 208) via the absorber canister 236. The absorber canister 236 removes carbon dioxide from the waste gas exhaled by the patient, for example. The fresh gas inlet 228 may include one or more flow control valves, such as a valve 238, for adjusting an amount (e.g., flow rate or concentration) of enriched fresh gas that is provided to the ABS 200, and therefore, to the patient. It may be understood that the enriched fresh gas may include one or more medical gases (e.g., oxygen, nitrogen, air, and nitrous oxide) with or without anesthetic agent (e.g., depending on whether or not the patient is anesthetized). For example, the valve 238 may be an electronically controlled, continuously variable valve that may be actuated into a plurality of positions between fully open and fully closed responsive to a command signal received from the controller 240. As the valve 238 is actuated to a further open position, enriched fresh gas flow through the fresh gas inlet 228 increases, and as the valve 238 is actuated to a further closed position, enriched fresh gas flow through the fresh gas inlet 228 decreases. In some examples, the controller 240 may adjust the position of the valve 238 based on feedback received from the air flow sensor 230 and/or the oxygen sensor 242.

ABS 200 may include additional valves, sensors, and gas inlets that are not shown in FIG. 2, such as various pressure relief and/or regulatory valves, pressure sensors, concentration sensors, and alternative fresh gas and/or oxygen inlets without departing from the scope of this disclosure. Thus, FIG. 2 may be understood to illustrate one embodiment of an example advanced breathing system that may provide mechanical ventilation to a patient.

FIG. 3 shows a cross-sectional schematic representation of an oxygen sensor 300, which may be the oxygen sensor 242 of FIG. 2, for example. The oxygen sensor 300 includes a sensor body 302, an electrolyte 304, an anode (or working electrode) 306 encircling a central portion of the sensor body 302, a cathode (or sensing electrode) 308 positioned on a top of the central portion of the sensor body 302, and a membrane 310. As an example, the anode 306 may be comprised of a base metal (e.g., lead or zinc), while the cathode 308 may be comprised of a noble metal (e.g., gold or platinum). The electrolyte 304 may be a basic electrolytic solution or gel that bathes the anode 306 and the cathode 308. As one example, the electrolyte 304 may be a solution of potassium hydroxide. As another example, the electrolyte 304 may be a solution of potassium hydroxide. Further, in some examples, the electrolyte 304 may be buffered, enabling it to resist pH changes.

The membrane 310 may form a diffusion barrier that limits or controls an amount of oxygen that enters the oxygen sensor 300 from a gas flow exterior to the membrane 310. Oxygen that permeates the membrane 310 and diffuses into the oxygen sensor 300 is dissociated and reduced to hydroxyl ions at the cathode 308. The membrane 310 provides a diffusion barrier that controls the amount of oxygen that reaches the cathode to an amount that can be fully reduced without significant delay. The hydroxyl ions created at the cathode 308 diffuse through the electrolyte 304 and oxide the anode 306. This process produces an electrical current that flows through a circuit formed between the cathode 308, the electrolyte 304, and the anode 306, with an amount of current generated proportional to an amount of oxygen consumed at the cathode 308, which is proportional to the amount (e.g., partial pressure) of the gas outside of the membrane 310.

Therefore, the oxygen sensor 300 further includes a first wire 312 that couples the cathode 308 to a measurement circuit via a first port 316 and a second wire 314 that couples the anode 306 to the measurement circuit via a second port 318. The measurement circuit includes a meter 320, which may be an ammeter configured to measure current in the circuit or a voltmeter configured to measure a voltage across the cathode 308 and the anode 306, for example. The meter 320 may transmit the voltage (or current) to a controller (e.g., the controller 240 of FIG. 2), and the controller may use the output voltage (or current) to determine the concentration of oxygen in the gas outside of the membrane 310 based on instructions stored in memory. Note that the oxygen sensor 300 may include fewer, alternative, or additional components, such as a moisture barrier, filters, and a circuit switch, and the example shown is one illustrative example of an electro-galvanic fuel cell-type (e.g., electrochemical) oxygen sensor.

Because the anode 306 is oxidized, the anode 306 is consumed while the sensor (e.g., the cathode 308) is exposed to an oxygen-containing gas. Over time, an amount of unoxidized base metal decreases at the anode 306, and an amount of oxidized base metal increases accordingly. The amount of oxidized base metal increases until the anode 306 is consumed (e.g., the anode 306 is entirely oxidized). When the anode 306 is entirely oxidized (e.g., all available surface area of the anode 306 is oxidized, with no unoxidized surface area remaining), the electrochemical reduction of the oxygen at the cathode 308 and the oxidation of the anode 306 no longer occurs. As a result, the current (or voltage) output of the oxygen sensor 300 is reduced to zero, and the oxygen sensor 300 no longer provides an output that is proportional to the amount of oxygen in the gas flow.

Therefore, FIG. 4 shows an example method 400 for monitoring an output of an oxygen sensor, such as the oxygen sensor 242 of FIG. 2, and estimating its end-of-life date (EOL) based on the output. The oxygen sensor may be positioned in a gas flow passage of a medical gas flow device, such as the inspiratory passage 218 shown in FIG. 2. The medical gas flow device may be an anesthesia machine, a ventilator, or an incubator, for example. Method 400 may be used to track the oxygen sensor output over time in order to identify sensor aging-related changes (e.g., decreases) in the output caused by consumption of a sensor anode, as described above. Method 400 may be executed by a controller, such as the controller 140 of FIG. 1 and/or the controller 240 of FIG. 2, according to instructions stored in a memory of the controller(s) and in conjunction with one or more inputs, such as the input received from the oxygen sensor and/or a human-machine interface (e.g., the HMI 143 of FIG. 1). Further, the controller may employ actuators (e.g., the valve 238 of FIG. 2) to adjust a medical gas flow according to the method described below.

At 402, method 400 includes calibrating the oxygen sensor. For example, the oxygen sensor may be regularly calibrated as part of a nominal maintenance procedure for the medical gas flow device. Calibrating the oxygen sensor includes obtaining an oxygen sensor reading (e.g., measurement) at 21% oxygen (e.g., a first oxygen concentration) at a first frequency, as indicated at 404, and obtaining an oxygen sensor reading at 100% oxygen (e.g., a second oxygen concentration) at a second frequency, as indicated at 406. For example, the controller may execute a calibration routine to obtain the oxygen sensor reading at 21% oxygen and the oxygen sensor reading at 100% oxygen. Because ambient air has approximately 21% oxygen, obtaining the oxygen sensor reading at 21% oxygen includes flowing air (e.g., medical air) through the gas flow passage and measuring the corresponding sensor voltage (or current) output, while obtaining the oxygen sensor reading at 100% oxygen includes flowing substantially pure oxygen gas (as supplied from a gas-holding cylinder, a pipeline, or generated via an oxygen compressor, for example) through the gas flow passage and measuring the corresponding sensor voltage (or current) output. As one example, the controller may adjust a flow control valve and/or a gas selector in order to flow the air (e.g., a first gas) or the pure oxygen gas (e.g., a second gas) through the gas flow passage, and thus to the oxygen sensor being calibrated, during the calibration routine. In an alternative example, different gases and/or mixtures of gases may be used for the first gas and the second gas that have different oxygen concentrations.

The 21% oxygen calibration may be performed more frequently than the 100% oxygen calibration during the calibration routine, making the first frequency greater than the second frequency, at least in some examples. As one example, the first frequency may be once per week (e.g., every 7 days), and the second frequency may be once per month (e.g., every 30 days). For example, the second frequency may be lower than the first frequency in order to reduce an occurrence of exposing the oxygen sensor to the pure oxygen gas. Thus, in some examples, executing the calibration routine and calibrating the oxygen sensor at 402 results in two measurements being obtained at two different oxygen concentrations (e.g., one at 21% oxygen and the other at 100% oxygen), and in other examples, only one measurement is obtained at one oxygen concentration (e.g., 21% oxygen or 100% oxygen).

Further, the calibration routine may include obtaining high frequency oxygen sensor readings after beginning to flow the gas of the appropriate oxygen concentration (e.g., either air or pure oxygen gas) through the gas flow passage, and the oxygen sensor reading may be recorded responsive to the oxygen sensor output stabilizing. As an example, the oxygen sensor output may be considered to be stabilized when the sensor output remains within a threshold range over a plurality of readings (e.g., 5-15 readings). The threshold range corresponds to a percentage deviation in the oxygen sensor output within which the oxygen sensor output is substantially unchanged. As one example, obtaining high frequency oxygen sensor readings may include obtaining a plurality of oxygen sensor readings per second, such as every 100-300 milliseconds. In this way, an amount of time spent calibrating the oxygen sensor may be decreased, which may decrease the exposure of the oxygen sensor to the gases used for the calibration. By decreasing the exposure of the oxygen sensor to pure oxygen gas in particular, the life of the oxygen sensor may be extended.

At 408, method 400 includes determining if at least one of the calibration readings (e.g., obtained at 404 and/or 406) is less than or equal to a degradation threshold. The degradation threshold is a calibrated oxygen sensor output voltage below which it may be assumed that the oxygen sensor is not functioning. Further, the degradation threshold may be different for the different two oxygen concentrations and may be manufacturer-specific. For example, the degradation threshold may be higher for the sensor reading at 100% oxygen than the sensor reading at 21% oxygen. As one non-limiting example, the degradation threshold for the sensor reading at 21% oxygen (e.g., a first degradation threshold) may be in a range from 1-5 mV (e.g., 3 mV), and the degradation threshold for the sensor reading at 100% oxygen (e.g., a second degradation threshold) may be in a range from 8-12 mV (e.g., 10 mV).

If at least one reading is less than or equal to the corresponding degradation threshold for the corresponding oxygen concentration, method 400 proceeds to 410 and includes outputting an oxygen cell degradation alert. The oxygen cell degradation alert may be output via the HMI, for example. As an example, the oxygen cell degradation alert may include one or more of a visual (e.g., text-based) message and an audible message. The degradation alert may state that the oxygen sensor is not functional and recommend immediate replacement, for example. Method 400 then ends.

Returning to 408, if none of the readings is less than or equal to the corresponding degradation threshold, method 400 proceeds to 412 and includes storing the oxygen sensor calibration reading(s) with the date. For example, each oxygen sensor calibration reading may be timestamped according to the date and time at which it was recorded and input into a calibration log, which may be stored in a memory of the controller. Thus, each calibration reading may serve as a calibration time point. In some examples, a separate calibration log is used for each calibration concentration, such as a first calibration log for 21% oxygen and a second calibration log for 100% oxygen. In other examples, the timestamped oxygen sensor calibration readings for both 21% oxygen and 100% oxygen are stored in a single calibration log along with the oxygen concentration. Further, in some examples, the timestamped oxygen sensor calibration readings for both 21% oxygen and 100% oxygen may be normalized to account for the different output voltages at the different oxygen concentrations, as will be elaborated below (e.g., at 426) and with reference to FIG. 5. In such examples, both raw data (e.g., the measured sensor output voltage) and the normalized data are stored in the calibration log(s). The calibration log(s) may include one or more of a table and a graph, for example.

At 414, method 400 includes determining if the calibration is an initial calibration. The calibration may be considered an initial calibration if it is the first calibration performed for the installed oxygen sensor (e.g., a first calibration routine performed for the installed oxygen sensor). As one example, the controller may determine that the calibration performed at 402 is the initial calibration if the reading is at least a threshold percentage greater than the last stored reading at the given oxygen concentration. The threshold percentage refers to a non-zero percentage that distinguishes nominal fluctuations in the oxygen sensor output from output increases due to the increased electrochemical activity of a new sensor (e.g., 10%). As another example, the controller may additionally or alternatively receive an input from an operator (e.g., via the HMI) that confirms that a new oxygen sensor has been installed.

If the calibration is the initial calibration, method 400 proceeds to 416 and includes storing the oxygen sensor calibration reading(s) as initial reading(s). Because the calibration is an initial calibration, the oxygen sensor calibration reading at the given oxygen concentration(s) is the first and only recorded output voltage for the oxygen sensor. Therefore, the current calibration reading(s) cannot be compared with previously stored readings to track the sensor output over time, and method 400 ends. For example, method 400 may be repeated at the first frequency and the second frequency to perform subsequent oxygen sensor calibrations at the two different oxygen concentrations.

If the calibration is not an initial calibration, method 400 proceeds to 420 and includes determining if at least one of the readings is at least a threshold amount from the initial calibration for the corresponding oxygen percentage. The threshold amount is a pre-determined value or percentage change from the initial calibration. When the oxygen sensor output has changed from the initial calibration by at least the threshold amount, it may be assumed that the oxygen sensor is beginning to approach its end-of-life. For example, the threshold amount may distinguish nominal fluctuations in the sensor output from output decreases due to decreasing oxygen sensor electrochemical activity that occurs as an available surface area of unoxidized anode decreases. As one example, the threshold amount is 20%.

If none of the readings is at least the threshold amount from the initial calibration (e.g., the calibration reading(s) obtained at 402 are within the threshold amount from the initial calibration), method 400 proceeds to 422 and includes continuing tracking the oxygen sensor calibration readings over time. As will be illustrated below with respect to FIG. 5, the oxygen sensor output may remain relatively stable for a duration after installation, and thus, an end-of-life of the oxygen sensor may not be estimated because there is no discernable change in the oxygen sensor output. However, each calibration reading continues to be stored in the calibration log. Method 400 then ends.

If at least one reading is at least the threshold amount from the initial calibration (e.g., the calibration reading(s) obtained at 402 has decreased by the threshold amount from the initial calibration), method 400 proceeds to 424 and includes determining a rate of change in the sensor reading using the most recent previously recorded calibration for the corresponding oxygen percentage for each obtained calibration reading. The rate of change may be determined as a difference between the current oxygen sensor reading and the most recent previously obtained oxygen sensor calibration reading for the given oxygen percentage divided by an amount of time that has elapsed between the current reading and the previous reading (e.g., the frequency used for the calibration). Thus, the rate of change is equal to a slope of the measurement decrement between two contiguous calibration measurements (e.g., the current calibration measurement and the prior calibration measurement immediately preceding the current calibration measurement for the given oxygen concentration).

Determining the rate of change further includes normalizing the rate for each oxygen percentage, as indicated at 426. Normalizing the rate of change for each oxygen percentage may transform the data to a same scale, enabling data from the 21% oxygen calibration to be combined with data from the 100% oxygen calibration, as will be elaborated below. For example, the controller may normalize the rate of change for the 21% oxygen calibration and the rate of change for the 100% oxygen calibration by scaling each value according to instructions stored in memory. As one example, the controller may normalize the sensor measurements according to known normalization equations and then determine the normalized rates of change using the normalized measurements.

At 428, method 400 includes estimating the oxygen sensor end-of-life date using the determined rate(s) of change. The end-of-life date refers to an amount of time, such as a number of days or weeks, until the sensor output is expected to decrease to zero due to the anode being entirely consumed given the current rate of sensor output decrease. For example, the controller may extrapolate the end-of-life date using the current calibration reading and the corresponding rate of change. As mentioned above, in some examples, the controller may combine the normalized rate of change from the 21% oxygen calibration and the normalized rate of change from the 100% oxygen calibration, which may increase an accuracy of the determined end-of-life date. Further, in some examples, controller may use a weighted average for combining the rates of change for the 21% oxygen calibration and the 100% oxygen calibration. For example, the rate of change for the 21% oxygen calibration may be given a greater weight than the rate of change for the 100% oxygen calibration because the concentration of oxygen in air may be more consistent than the concentration of oxygen in the substantially pure oxygen, which may have a higher incidence of contamination (particularly when the oxygen is generated via an oxygen compressor). In some examples, the controller may additionally or alternatively determine the end-of-life date separately for the 21% oxygen calibration and the 100% oxygen calibration and then combined the determined end-of-life dates by averaging the values (e.g., either a weighted average or a non-weighted average). By combining the information given by the 21% oxygen calibration and the 100% oxygen calibration, a higher number of data points may be used, which may increase an accuracy of the estimated end-of-life.

At 430, method 400 optionally includes communicating the estimated end-of-life date to a remote server. The remote server may be communicatively connected to the controller via wired or wireless communication. The remote server may be monitored by an administrator of the medical gas flow device (e.g., a person or department that schedules supply ordering and maintenance for the medical gas flow device) and/or an oxygen sensor supplier. Thus, by communicating the end-of-life date to the remote server, the administrator and/or the oxygen sensor supplier may be able to anticipate an oxygen sensor replacement time. Because oxygen sensors cannot be stored for a prolonged period, communicating the oxygen sensor replacement time may decrease an occurrence of both oxygen sensor over-ordering, which may result in increased expenses, and under-ordering, which may result in downtime of the medical gas flow device.

At 432, method 400 includes determining if the estimated end-of-life date is less than a threshold duration. The threshold duration refers to a pre-determined non-zero time duration stored in a memory of the controller below which, if not promptly ordered, the oxygen sensor replacement may not be received before the current oxygen sensor no longer functions. As one non-limiting example the threshold duration is 15 days.

If the estimated end-of-life date is not less than the threshold duration, method 400 proceeds to 434 and includes outputting an oxygen sensor replacement notification having a lower priority (e.g., a first oxygen sensor replacement notification). Because there is still a cushion of time before the end-of-life date, the lower priority notification may be a text-based (e.g., visual) message output to a display of the HMI, for example, that includes instructions for replacing the oxygen sensor in less than 90 days. In some examples, the estimated end-of-life date may be displayed and decremented each passing day. Further, the end-of-life date may be updated as new calibration readings are obtained. Method 400 then ends. For example, at least parts of method 400 may be repeated daily, such as to determine whether the estimated end-of life date has decreased below the threshold duration.

Returning to 432, if the estimated end-of-life date is less than the threshold duration, method 400 proceeds to 436 and includes outputting an oxygen sensor replacement notification having a higher priority (e.g., a second oxygen sensor replacement notification). The higher priority notification may include both a text-based, visual message and an audible alarm and/or message output via the HMI. The higher priority notification may suggest replacing the oxygen sensor in less than 15 days, for example. Further, the estimated end-of-life data may be displayed on the display screen of the HMI and decremented each passing day. Further still, in some examples, the controller may communicate with the remote server to automatically submit an oxygen sensor replacement order and/or request an oxygen sensor replacement (e.g., if one has not already been ordered) responsive to the estimated end-of-life date decreasing below the threshold duration. Method 400 then ends.

In this way, the oxygen sensor end-of-life date may be predicted based on changes in the output of the oxygen sensor. Because the time it takes to consume the anode of each oxygen sensor varies based on, for example, oxygen exposure conditions, determining the end-of-life of the oxygen sensor based on the output of the sensor itself enables the sensor to be replaced when the sensor is used up. By replacing the sensor when the sensor is used up instead of pre-emptively (based on an average consumption time, for example), oxygen sensor costs may be decreased. Further, by predicting the end-of-life date of the oxygen sensor, a replacement oxygen sensor may be readily available, reducing downtime of the medical gas flow device due to not having the oxygen sensor.

Next, FIG. 5 shows an example graph 500 of tracking oxygen sensor calibration measurements over time and extrapolating an end-of life date from a change in the oxygen sensor calibration measurements. The oxygen sensor is included in a gas flow passage of a medical gas flow device, such as the oxygen sensor 242 of the ABS 200 shown in FIG. 2, for example. Further, the oxygen sensor calibration measurements may be tracked by a controller, such as the controller 240 of FIG. 2. A plot 502, represented by a thinner solid line and smaller filled circles, shows calibration measurements for 21% oxygen (e.g., a first oxygen concentration), and a plot 504, represented by a thicker dashed line and larger filled circles, shows calibration measurements for 100% oxygen. Each filled circle represents one calibration time point measurement at the corresponding oxygen concentration. Graph 500 includes time as the horizontal axis and a normalized oxygen sensor output voltage on the vertical axis, enabling measurements from the 21% oxygen calibration (plot 502) and the 100% oxygen calibration (plot 504) to be displayed on graph 500. Thus, in the example shown, the initial calibration measurement for each oxygen percentage, obtained at time $t_0$, is set to a same value.

In the example shown, the 21% oxygen calibration measurement (plot 502) is obtained at a higher frequency than the 100% oxygen calibration measurement (plot 504). Specifically, a first duration $\Delta t1$ elapses between each 21% oxygen (e.g., first oxygen concentration) calibration measurement, whereas a second duration $\Delta t2$ elapses between each 100% oxygen (e.g., second oxygen concentration) calibration measurement. Thus, one 21% oxygen calibration measurement is obtained every first duration $\Delta t1$, and one 100% oxygen calibration measurement is obtained every second duration $\Delta t2$. In the present example, $\Delta t2$ is four times as long as $\Delta t1$. For example, $\Delta t1$ may be one week (e.g., 7 days), whereas $\Delta t2$ is four weeks (e.g., 28 days).

Graph 500 also shows a threshold 506, which corresponds to the threshold amount from the initial calibration described above with respect to 420 of FIG. 4. Thus, normalized oxygen sensor output voltages above the threshold 506 are tracked without estimating an end-of-life date of the oxygen sensor, as the oxygen sensor output remains relatively high. In the example shown the normalized oxygen sensor output remains substantially unchanged from the initial calibration reading obtained at t0 for the first thirteen measurements at 21% oxygen (plot 502) and the first four measurements at 100% oxygen (plot 504). At time t1, the 21% oxygen calibration measurement begins to decrease (plot 502) but remains above the threshold 506. Thus, the end-of-life is not estimated at time t1.

However, the 21% oxygen calibration measurement (plot 502) obtained at time t2 is less than the threshold 506. In response, the controller estimates the end-of-life date of the oxygen sensor based on a rate of change in the oxygen sensor output between the most recent previously recorded 21% oxygen reading (e.g., obtained at time t1) and the current reading (e.g., obtained at time t2). The controller extrapolates this rate of change as a slope of a line 508 to determine when the oxygen sensor output will decrease to zero. The resulting end-of-life date estimate, $EOL1_{21\%}$, is shown where the line 508 intersects with the horizontal axis.

Between time t2 and time t3, the 21% oxygen calibration measurements continue to be obtained every $\Delta t1$. The controller updates the estimated end-of-life date based on a new rate of change calculated between each current measurement and the previously recorded 21% oxygen calibration measurement. However, between time t2 and time t3, the rate of change, and thus the estimated end-of-life date, does not change and remains at $EOL1_{21\%}$.

At time t3, the first 100% oxygen calibration measurement that is less than the threshold 506 is obtained (plot 504). In response, the controller estimates an end-of-life date based on a rate of change between the current 100% oxygen calibration measurement (e.g., obtained at time t3) and the most recent previously obtained 100% oxygen calibration measurement (e.g., obtained shortly before time t1). The controller extrapolates this rate of change as a slope of a line 510 to determine when the oxygen sensor output will decrease to zero. The resulting end-of-life date estimate, $EOL1_{100\%}$, is shown where the line 510 intersects with the horizontal axis. $EOL1_{100\%}$ is later than $EOL1_{21\%}$, which does not change based on the 21% oxygen calibration measurement obtained at t3. Therefore, in some examples, the controller averages $EOL1_{21\%}$ and $EOL1_{100\%}$ to increase an accuracy of the end-of-life date estimation. Further, the average may be weighted toward $EOL1_{21\%}$ due to the potential increased accuracy of the 21% oxygen calibration measurement.

At time t4, the rate of change between the current 21% oxygen calibration measurement (e.g., obtained at time t4) and the most recent prior 21% oxygen calibration measurement (e.g., obtained between time t3 and time t4) changes. The rate at which an anode of the oxygen sensor is consumed may change due to changes in the overall amount of oxygen the oxygen sensor is exposed to between the 21% oxygen calibration measurements, for example. The controller estimates an updated end-of-life date, $EOL2_{21\%}$, by extrapolating a line 512 based on the new rate of change between the 21% oxygen calibration measurements. $EOL2_{21\%}$ is later date than $EOL1_{21\%}$ and may be averaged with $EOL1_{100\%}$, as described above.

A new 100% oxygen calibration measurement is obtained after time t4. The rate of change between the current 21% oxygen calibration measurement (obtained just after time t4) and the previous 21% oxygen calibration measurement (obtained at time t3) is different, resulting in an updated estimated end-of-life date $EOL2_{100\%}$ from the intersection of the horizontal axis and a line 514, which includes an updated slope to reflect the new rate of change in the oxygen sensor output. $EOL2_{100\%}$ is sooner than $EOL1_{100\%}$ and is closer to $EOL2_{21\%}$ than $EOL1_{100\%}$ was to $EOL1_{21\%}$. Thus, the data from both the 21% oxygen calibration measurements (plot 502) and the 100% oxygen sensor calibration measurements (plot 504) may converge as more data is obtained, at least in some examples.

Thus, the systems and methods described herein provide for accurately estimating an end-of-life date of an oxygen sensor in a medical device. In particular, because each oxygen sensor will be depleted at a different rate depending on the particular oxygen exposure conditions of each oxygen sensor, the systems and methods described herein enable the end-of-life date of each oxygen sensor to be determined based on the output of the oxygen sensor itself. As a result, a replacement oxygen sensor may be ordered in a timely fashion, which may reduce an amount of down time of the medical device due to loss of oxygen sensor functionality. Further, premature oxygen sensor replacement may be decreased, which may decrease maintenance costs of the medical device. Further still, by communicating oxygen sensor status information to a remote server that may be monitored by a manufacturer/supplier of the oxygen sensor, oxygen sensor manufacturing logistics may be more efficiently coordinated so that oxygen sensor manufacturing more closely meets oxygen sensor demand and reduces the time the sensor sits on a shelf. Overall, customer satisfaction may be increased.

A technical effect of estimating an end-of-life date of an oxygen sensor of a medical device based on calibration readings of the oxygen sensor is that the oxygen sensor can be used until substantially depleted while reducing downtime of the medical device due to unexpected oxygen sensor depletion.

In an embodiment, a method for a medical gas flow device comprises: tracking an output of an oxygen sensor during calibration over time; and responsive to the output decreasing by at least a threshold amount from an initial calibration output, estimating an end-of-life date of the oxygen sensor and outputting a replacement notification. In examples, tracking the output of the oxygen sensor during the calibration over time includes calibrating the oxygen sensor at a first oxygen concentration at a first frequency and calibrating the oxygen sensor at a second oxygen concentration at a second frequency, less than the first frequency. In some examples, the first oxygen concentration is less than the second oxygen concentration, and tracking the output of the oxygen sensor during the calibration over time further includes: while flowing a first gas having the first oxygen concentration through the medical gas flow device, obtaining high frequency sensor readings and recording the output of the oxygen sensor as a first oxygen concentration calibration measurement responsive to the output of the oxygen sensor stabilizing during the high frequency sensor readings; and while flowing a second gas having the second oxygen concentration through the medical gas flow device, obtaining the high frequency sensor readings and recording the output of the oxygen sensor as a second oxygen concentration calibration measurement responsive to the output of the oxygen sensor stabilizing during the high frequency sensor readings. In one example, estimating the end-of-life date of the oxygen sensor includes averaging a first end-of-life date determined based on the first oxygen concentration calibration measurement and a second end-of-life date determined based on the second oxygen concentration calibration measurement.

In some examples, the end-of-life date is a date at which the output of the oxygen sensor decreases to zero, and estimating the end-of-life date of the oxygen sensor comprises: determining a rate of change in the output of the oxygen sensor during the calibration; and extrapolating the end-of-life date using the rate of change. In an example, determining the rate of change in the output of the oxygen sensor during the calibration comprises: determining a difference between the output of the oxygen sensor at a current calibration time point and the output of the oxygen sensor at a prior calibration time point immediately before the current calibration time point; and dividing the difference by an amount of time between the prior calibration time point and the current calibration time point. In examples, outputting the replacement notification comprises: outputting a first notification having a lower priority responsive to the end-of-life date being greater than a threshold duration; and outputting a second notification having a higher priority responsive to the end-of-life date being less than the threshold duration. For example, the first notification includes only a visual message, and the second notification includes the visual message and an audible message.

In an example, the method further comprises communicating the end-of-life date to a remote monitoring server communicatively coupled to the medical gas flow device.

In another embodiment, a method for an anesthesia machine comprises: calibrating an oxygen sensor, including obtaining an oxygen sensor reading at one or more concentrations of oxygen; estimating an end-of-life date of the oxygen sensor responsive the oxygen sensor reading being at least a threshold amount from an initial calibration reading; outputting a first replacement notification responsive to the end-of-life date being greater than a threshold duration; and outputting a second replacement notification responsive to the end-of-life date being less than the threshold duration. In examples, obtaining the oxygen sensor reading at one or more concentrations of oxygen comprises obtaining a first oxygen sensor reading at a first concentration of oxygen and a second oxygen sensor reading at a second concentration of oxygen, greater than the first concentration of oxygen. In some examples, estimating the end-of-life date comprises: estimating a first end-of-life date based on a first rate of change in the first oxygen sensor reading between a current calibration and a most recent previous calibration at the first concentration of oxygen; estimating a second end-of-life date based on a second rate of change in the second oxygen sensor reading between the current calibration and a most recent previous calibration at the second concentration of oxygen; and determining the end-of-life date based on at least one of the first end-of-life date and the second end-of-life date. In an example, determining the end-of-life date based on at least one of the first end-of-life date and the second end-of-life date includes one of selecting the first end-of-life date, averaging the first end-of-life date and the second end-of-life date, and performing a weighted average of the first end-of-life date and the second end-of-life date.

In an example, the threshold amount is a pre-determined percentage of the initial calibration reading. In one example, outputting the first replacement notification includes outputting a visual message to a display, and outputting the second replacement notification includes outputting the visual message to the display and outputting an audible alert via a speaker.

In an example, the method further comprises: responsive to the end-of-life date being less than the threshold duration, submitting an oxygen sensor replacement order to a remote server.

In another embodiment, a system for a medical gas flow device, comprises: an inspiratory flow passage configured to flow gas from a gas source to a patient breathing circuit; an oxygen sensor positioned in the inspiratory flow passage; and a controller including instructions stored in non-transitory memory that, when executed, cause the controller to: record an output voltage of the oxygen sensor during a calibration routine performed at a pre-determined frequency; and monitor depletion of the oxygen sensor by tracking the output voltage recorded during the calibration routine over time.

In an example, the oxygen sensor is an electro-galvanic oxygen sensor comprising an anode and a cathode bathed in an electrolyte, the electrolyte electrically coupling the anode to the cathode, and a measurement circuit electrically coupled to the anode and the cathode.

In some examples, to monitor the depletion of the oxygen sensor by tracking the output voltage recorded during the calibration routine over time, the controller includes further instructions stored in non-transitory memory that, when executed, cause the controller to: extrapolate an end-of-life date of the oxygen sensor based on a change in the output voltage between contiguous executions of the calibration routine responsive to the output voltage decreasing by a threshold from an initial output voltage of the oxygen sensor recorded during a first calibration routine. In an example, the system further comprises a human-machine interface communicatively coupled to the controller, the human-machine interface including a display and a speaker, and the controller includes further instructions stored in non-transitory memory that, when executed, cause the controller to: output a lower priority oxygen sensor replacement notification via the human-machine interface responsive to the extrapolated end-of-life date being greater than a threshold duration, the lower priority oxygen sensor replacement notification including text-based instructions displayed on the display; and output a higher priority oxygen sensor replacement notification via the human-machine interface responsive to the extrapolated end-of-life date being less than the threshold duration, the higher priority oxygen sensor replacement notification including both text-based instructions displayed on the display and an audible message communicated via the speaker.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for a medical gas flow device, comprising:
controlling at least one valve of the medical gas flow device to flow a first gas having a first oxygen concentration through an inspiratory flow passage having an oxygen sensor, and detecting, by the oxygen sensor, a first oxygen concentration calibration measurement at a first frequency;
controlling the at least one valve of the medical gas flow device to flow a second gas having a second oxygen concentration through the inspiratory flow passage having the oxygen sensor, and detecting, by the oxygen sensor, a second oxygen concentration calibration measurement at a second frequency that is less than the first frequency; and
responsive to the second oxygen concentration calibration measurement decreasing by at least a threshold amount from the first oxygen concentration calibration measurement, estimating an end-of-life date of the oxygen sensor and outputting a replacement notification on a display of the medical gas flow device,
wherein estimating the end-of-life date of the oxygen sensor includes averaging a first end-of-life date determined based on the first oxygen concentration calibration measurement and a second end-of-life date determined based on the second oxygen concentration calibration measurement.

2. The method of claim 1, wherein the first oxygen concentration is less than the second oxygen concentration, and wherein detecting the first and second oxygen concentration calibration measurements further includes:
while flowing the first gas having the first oxygen concentration through the inspiratory flow passage, obtaining high frequency sensor readings and recording the first oxygen concentration calibration measurement responsive to the first oxygen concentration stabilizing during the high frequency sensor readings; and
while flowing the second gas having the second oxygen concentration through the inspiratory flow passage, obtaining the high frequency sensor readings and recording the second oxygen concentration calibration measurement responsive to the second oxygen concentration stabilizing during the high frequency sensor readings.

3. The method of claim 1, wherein the end-of-life date is a date at which the output of the oxygen sensor decreases to zero, and estimating the end-of-life date of the oxygen sensor comprises:
determining a rate of change in the first and second oxygen concentration calibration measurements; and
extrapolating the end-of-life date using the rate of change.

4. The method of claim 3, wherein determining the rate of change in the output of the oxygen sensor during the calibration comprises:
determining a difference between a current calibration time point and a prior calibration time point immediately before the current calibration time point; and
dividing the difference by an amount of time between the prior calibration time point and the current calibration time point.

5. The method of claim 3, wherein outputting the replacement notification comprises:
outputting a first notification having a lower priority responsive to the end-of-life date being greater than a threshold duration; and
outputting a second notification having a higher priority responsive to the end-of-life date being less than the threshold duration.

6. The method of claim 5, wherein the first notification includes only a visual message, and the second notification includes the visual message and an audible message.

7. The method of claim 1, further comprising communicating the end-of-life date to a remote monitoring server communicatively coupled to the medical gas flow device.

8. A method for an anesthesia machine, comprising:
controlling at least one valve of the anesthesia machine to flow a first gas having a first oxygen concentration through an inspiratory flow passage having an oxygen sensor, and detecting, by the oxygen sensor, a first oxygen concentration calibration measurement at a first frequency;
controlling the valve of the anesthesia machine to flow a second gas having a second oxygen concentration through the inspiratory flow passage having the oxygen sensor, and detecting, by the oxygen sensor, a second oxygen concentration calibration measurement at a second frequency that is less than the first frequency;
estimating an end-of-life date of the oxygen sensor responsive to the second oxygen concentration calibration measurement being at least a threshold amount from the first oxygen concentration calibration measurement;
outputting a first replacement notification responsive to the end-of-life date being greater than a threshold duration; and
outputting a second replacement notification responsive to the end-of-life date being less than the threshold duration,
wherein the second oxygen concentration is greater than the first oxygen concentration, and
wherein estimating the end-of-life date comprises:
estimating a first end-of-life date based on a first rate of change in the first oxygen concentration calibration measurement between a current calibration and a most recent previous calibration at the first oxygen concentration;
estimating a second end-of-life date based on a second rate of change in the second oxygen concentration calibration measurement between the current calibration and a most recent previous calibration at the second oxygen concentration; and
determining the end-of-life date based on both of the first end-of-life date and the second end-of-life date.

9. The method of claim 8, wherein determining the end-of-life date based on both of the first end-of-life date and the second end-of-life date includes one of selecting the first end-of-life date, averaging the first end-of-life date and the second end-of-life date, and performing a weighted average of the first end-of-life date and the second end-of-life date.

10. The method of claim 8, wherein the threshold amount is a pre-determined percentage of first oxygen concentration calibration measurement.

11. The method of claim 8, wherein outputting the first replacement notification includes outputting a visual message to a display, and outputting the second replacement notification includes outputting the visual message to the display and outputting an audible alert via a speaker.

12. The method of claim 8, further comprising:
responsive to the end-of-life date being less than the threshold duration, submitting an oxygen sensor replacement order to a remote server.

13. A system for a medical gas flow device, comprising:
an inspiratory flow passage configured to flow a first gas and a second gas from at least one gas source to a patient breathing circuit;
one or more valves configured to control flow of the first gas and the second gas through the inspiratory flow passage;
an oxygen sensor positioned in the inspiratory flow passage;
a display configured to display information; and
a controller including instructions stored in non-transitory memory that, when executed, cause the controller to:
control the one or more valves to provide a first flow of the first gas having a first oxygen concentration through the inspiratory flow passage;
detecting a first voltage output by the oxygen sensor during the first flow;
control the one or more valves to provide a second flow of the second gas having a second oxygen concentration through the inspiratory flow passage;
detecting a second voltage output by the oxygen sensor during the second flow; and
monitor depletion of the oxygen sensor by tracking the output voltage recorded during the calibration routine over time by extrapolating an end of life date of the oxygen sensor based on a difference between the first voltage and the second voltage;
control the display to output a lower priority oxygen sensor replacement notification based on the extrapolated end-of-life date being greater than a threshold duration; and control the display to output a higher priority oxygen sensor replacement notification responsive to the extrapolated end-of-life date being less than the threshold duration.

14. The system of claim 13, wherein the oxygen sensor is an electro-galvanic oxygen sensor comprising an anode and a cathode bathed in an electrolyte, the electrolyte electrically coupling the anode to the cathode, and a measurement circuit electrically coupled to the anode and the cathode.

15. The system of claim 13, further comprising a human-machine interface communicatively coupled to the controller, the human-machine interface including a display and a speaker, and wherein the controller includes further instructions stored in the non-transitory memory that, when executed, cause the controller to:
output the lower priority oxygen sensor replacement notification via the human-machine interface responsive to the extrapolated end-of-life date being greater than the threshold duration, the lower priority oxygen sensor replacement notification including text-based instructions displayed on the display; and
output the higher priority oxygen sensor replacement notification via the human-machine interface responsive to the extrapolated end-of-life date being less than the threshold duration, the higher priority oxygen sensor replacement notification including both the text-based instructions displayed on the display and an audible message communicated via the speaker.

* * * * *